US011338132B2

(12) United States Patent
Ko (10) Patent No.: US 11,338,132 B2
(45) Date of Patent: May 24, 2022

(54) TREATMENT DEVICE USING HIGH FREQUENCY (71) Applicant: LUTRONIC CORPORATION, Goyang (KR)

(72) Inventor: Kwang Chon Ko, Paju (KR)

(73) Assignee: LUTRONIC CORPORATION, Goyang (KR)

(*) Notice: Subject to any disclaimer, the term of this patent is extended or adjusted under 35 U.S.C. 154(b) by 1063 days.

(21) Appl. No.: 15/965,626

(22) Filed: Apr. 27, 2018

(65) Prior Publication Data

US 2018/0243553 A1 Aug. 30, 2018

Related U.S. Application Data (63) Continuation of application No. 14/360,494, filed as application No. PCT/KR2012/010074 on Nov. 26, 2012, now abandoned.

(30) Foreign Application Priority Data

Nov. 24, 2011 (KR) .................. 10-2011-0123800

(51) Int. Cl.
*A61B 18/14* (2006.01)
*A61N 1/06* (2006.01)
(Continued)

(52) U.S. Cl.
CPC ............ *A61N 1/06* (2013.01); *A61B 18/1477* (2013.01); *A61N 1/328* (2013.01);
(Continued)

(58) Field of Classification Search
CPC ...... A61B 18/1477; A61B 2018/00452; A61B 2018/128; A61B 2018/00464;
(Continued)

(56) References Cited

U.S. PATENT DOCUMENTS 5,871,524 A * 2/1999 Knowlton ......... A61M 15/0036
607/101
6,413,255 B1 * 7/2002 Stern .................... A61B 18/14
606/41
(Continued)

FOREIGN PATENT DOCUMENTS

KR 86-3030 5/1986
KR 10-200-90084522 A 5/2009
(Continued)

OTHER PUBLICATIONS

International Search Report for PCTIKR2012/010074 dated Feb. 15, 2013.

*Primary Examiner* — Michael F Peffley (57) ABSTRACT

A treatment device using a high frequency according to the present invention includes: a plurality of electrodes which transfers high frequency energy to the skin; a plurality of pads each of which is provided on one surface thereof with at least one of the electrodes; and a plurality of elastic members which independently and elastically support the other surfaces of the plurality of pads, respectively, so that plurality of electrodes can be three-dimensionally and closely attached to the curved surface of the skin. Accordingly, even when treating a body region having many curves, the attachment of the electrodes is efficiently maintained. In addition, although a hand piece moves in a state in which the plurality of pads are attached to skin, the plurality of pads can be maintained in the skin attached state while actively coping with the curves.

19 Claims, 11 Drawing Sheets

(51) Int. Cl.
   *A61N 1/32*    (2006.01)
   *A61B 18/12*   (2006.01)
   *A61F 7/00*    (2006.01)
   *A61B 18/00*   (2006.01)

(52) U.S. Cl.
   CPC ............... *A61B 2018/00452* (2013.01); *A61B 2018/128* (2013.01); *A61F 2007/0052* (2013.01)

(58) Field of Classification Search
   CPC .... A61B 2018/0047; A61B 2018/0016; A61B 2018/00107; A61F 2007/0052; A61N 1/06; A61N 1/328
   See application file for complete search history.

(56) References Cited

U.S. PATENT DOCUMENTS

| | | | | |
|---|---|---|---|---|
| 7,794,461 | B2 * | 9/2010 | Eder | A61B 18/1442 606/51 |
| 8,882,758 | B2 * | 11/2014 | Nebrigic | A61B 18/14 606/33 |
| 2008/0140069 | A1 * | 6/2008 | Filloux | A61B 18/1492 606/41 |
| 2008/0200969 | A1 * | 8/2008 | Weber | A61N 1/06 374/E13.002 |

FOREIGN PATENT DOCUMENTS

| | | |
|---|---|---|
| KR | 10-2010-0090486 A | 8/2010 |
| WO | WO 2007057930 A1 | 5/2007 |

* cited by examiner

TREATMENT DEVICE USING HIGH FREQUENCY

CROSS REFERENCE TO RELATED APPLICATIONS

The present invention is a continuation of and claims priority to U.S. application Ser. No. 14/360,494 filed May 23, 2014, now abandoned, which is a U.S. National Stage of International Patent Application No. PCT/KR2012/010074 filed Nov. 26, 2012, which claims priority to and the benefit of Korean Patent Application No. 10-2011-0123800 filed in the Korean Intellectual Property Office on Nov. 24, 2011, the entire contents of which are incorporated herein by reference.

TECHNICAL FIELD

The present invention relates to a treatment device using a radio frequency, and more particularly to a treatment device using a radio frequency that can treat skin tissues, using RF energy.

BACKGROUND ART

Recently, technologies of treating skins by changing the tissue state of the skins or improving the tissue characteristics by providing energy to the skins, using various energy sources have been popularized. Skin treatment devices using various energy sources such as a laser beam, a flash lamp, or supersonic waves have been developed, and recently, researches about a skin treatment device using RF RF energy has been actively conducted.

When RF energy is provided to a skin surface, the molecules of a skin tissue vibrate and rub each other every time the current direction of the radio frequency changes, such that deep heat is generated due to rotation, torsion, and collision of the molecules. The deep heat increases the temperature of the skin tissue and reorganizes a collagen layer, such that wrinkles can be improved and skin elasticity can be increased. Further, the blood circulation in the skin tissue is increased and accelerated, such that the overall state of the skin is improved, including skin anti-aging.

A treatment device using a radio frequency has been disclosed in Korean Patent Application Publication No. 2010-0090486 (published on 16 Aug. 2010).

In the treatment device using a radio frequency, electrodes transmitting RF energy are horizontally arranged or the installation sides of the electrodes are fixed, such that when treating the portions of a body which have many curves such as the face with the device, it is difficult to uniformly treat the portions, because only some of the electrodes come in contact with the skin.

DISCLOSURE

Technical Problem

The present invention has been made in an effort to provide a treatment device using a radio frequency that is useful even for portions of a body which have many curves.

Technical Solution

A treatment device using a radio frequency according to an aspect of the present invention includes: a plurality of electrodes that transmits RF energy to a skin; a plurality of pads where at least one or more of the electrodes are disposed on one side; and a plurality of elastic members that independently and elastically supports the other sides of the pads so that the electrodes can be three-dimensionally brought in close contact with a curved surface of the skin.

A treatment device using a radio frequency according to another embodiment of the present invention includes: a body that includes a radio frequency generator generating RF energy; and a handpiece that includes a plurality of electrodes electrically connected with the radio frequency generator and transmitting the RF energy to a skin, on one end, in which the handpiece includes a plurality of pads where the electrodes are disposed and a plurality of elastic members that independently and elastically supports the pads so that the electrodes are three-dimensionally brought in close contact with curved surfaces of a skin.

Flexible elastic portions may be disposed between the pads.

The pad may have a mounting groove on one side where the electrode is disposed.

The pads may include a center pad at the center and peripheral pads around the center pad.

The electrodes may include a first electrode and second electrodes which have different polarities, the first electrode may be disposed on the center pad, and the second electrodes may be disposed on the peripheral pads.

The electrodes may include a first electrode module, a second electrode module, and a third electrode module which provide RF energies at different frequencies, an anode and a cathode of the first electrode module may be disposed on the center pad, an anode and a cathode of the second electrode module may be disposed on the pads, which are positioned left and right from the center pad, respectively, in the peripheral pads, and an anode and a cathode of the third electrode module may be disposed on the pads, which are positioned over and under the center pad, respectively, in the peripheral pads.

The electrodes may include a first electrode and second electrodes which provide RF energies at different frequencies, an anode and a cathode of the first electrode may be disposed on the center pad, and anodes and cathodes of the second electrodes may be disposed on the peripheral pads.

The pads may include an upper pad, a lower pad, a left pad, and a right pad.

The electrodes may include a first electrode and second electrodes which provide RF energies at different frequencies, an anode and a cathode of the first electrode may be disposed on the upper pad and the lower pad, and an anode and a cathode of the second electrodes may be disposed on the left pad and the right pad.

The pads may include a first pad and a second pad, the electrodes may include a first electrode unit and a second electrode unit that have different polarities, the first electrode unit may be disposed on the first pad, and the second electrode unit may be disposed on the second pad.

The electrodes may include a plurality of protruding electrodes of which the ends come in contact with a skin are formed in a spherical shape or a flat shape.

The electrodes may include a plurality of protruding electrodes that have needle-shaped ends and is partially inserted into a skin.

The elastic members may be coil springs having restoring force against compression force.

The treatment device may further include an elastic member support that is spaced from the pads and elastically support the elastic members.

A plurality of elastic member support pins where the elastic members are mounted may be formed on one side of the elastic member support.

Advantageous Effects

According to the treatment device using a radio frequency of the present invention, contact of the electrodes can be efficiently maintained even in treatment for parts with many curves of a human body. Further, even if the handpiece is moved in contact with a skin, it can actively cope with curves and the pad can keep in contact with the skin.

The technical effects of the present invention are not limited to those described above and other effects may be made apparent to those skilled in the art from the following description.

MODE FOR INVENTION

Hereinafter, embodiments of the present invention are described in detail with reference to the accompanying drawings. However, the present invention is not limited to the following embodiments, but may be implemented in various ways and the embodiment are provided to make the present invention clear and help those skilled in the art completely understand the present invention. The shapes of the components may be exaggerated to make the description clear in the drawings and the components indicated by the same reference numerals are the same in the drawings.

Figure 1:
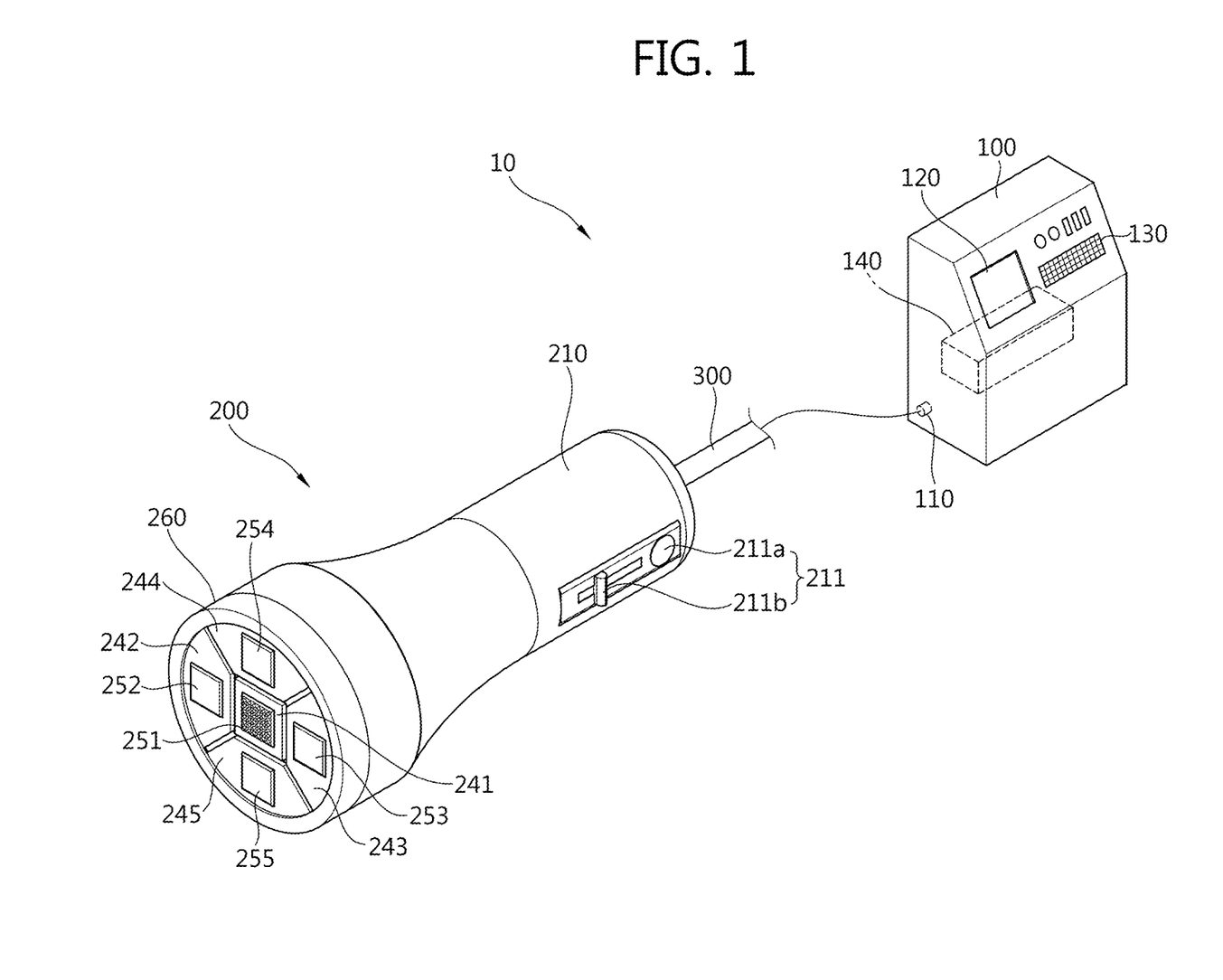
FIG. 1 is a perspective view showing a treatment device using a radio frequency according to the first embodiment of the present invention.

FIG. 1 is a perspective view showing a treatment device using a radio frequency according to the first embodiment of the present invention.

As shown in FIG. 1, a treatment device 10 using a radio frequency according to the first embodiment of the present invention includes a body 100, a handpiece 200, and a cable 300 connecting the body 100 with the handpiece 200.

The body 100 has a power supply 110 that can be supplied with power from the outside, and a control panel 130 for selecting the operational details of the treatment device and a display unit 120 showing the operational details to a user may be disposed on the outer side of the body 100. A radio frequency generator 140 that generates RF energy, using the power from the power supply 110 may be disposed inside the body 100. The radio frequency generator 140 may include a plurality of radio frequency generation modules 141, 142, and 143 (see FIG. 8) based on the kinds of frequencies to be able to generate RF energy at various frequencies.

The handpiece 200 has a body 210 and an electrode unit 250 (251~255).

The body 210 forms the external shape of the handpiece 200 and may have a structure that a user can hold with a hand in an operation. In the body 210, the electrode unit 250 may be disposed at one end and an operation unit 211 may be disposed on the outer side.

The operation unit 211, which is a component for a user to easily select the operational details of the treatment device in an operation, may have a switch 211a and a regulator that regulates RF energy transmitted a skin from the electrode unit 250. The electrode unit 250 is electrically connected with the radio frequency generator 140 of the body 100 and provides RF energy to a skin tissue in contact with the skin in an operation.

The cable 200 transmits the RF energy from the radio frequency generator 140 and can transmit various control signals between the body 100 and the handpiece 200.

The control signals may include a signal for controlling the handpiece 200 from the body 100 and a control signal from the operation unit 211 of the handpiece 200.

In this configuration, transmitting lines 310 (see FIG. 8) for transmitting RF energy and a signal line 320 for transmitting various control signals may be separately formed.

Although the body 100 and the handpiece 200 are separated in FIG. 1, the body 100 may be disposed inside the handpiece 200. For example, the radio frequency generator 140 may be disposed in the handpiece 200. Further, the operation unit 211 may have the function of the control panel 130 and the display unit 120 may also be disposed on the outer side of the handpiece 200.

The handpiece of the treatment device using a radio frequency according to the first embodiment of the present invention is described in detail hereafter.

Figure 2:
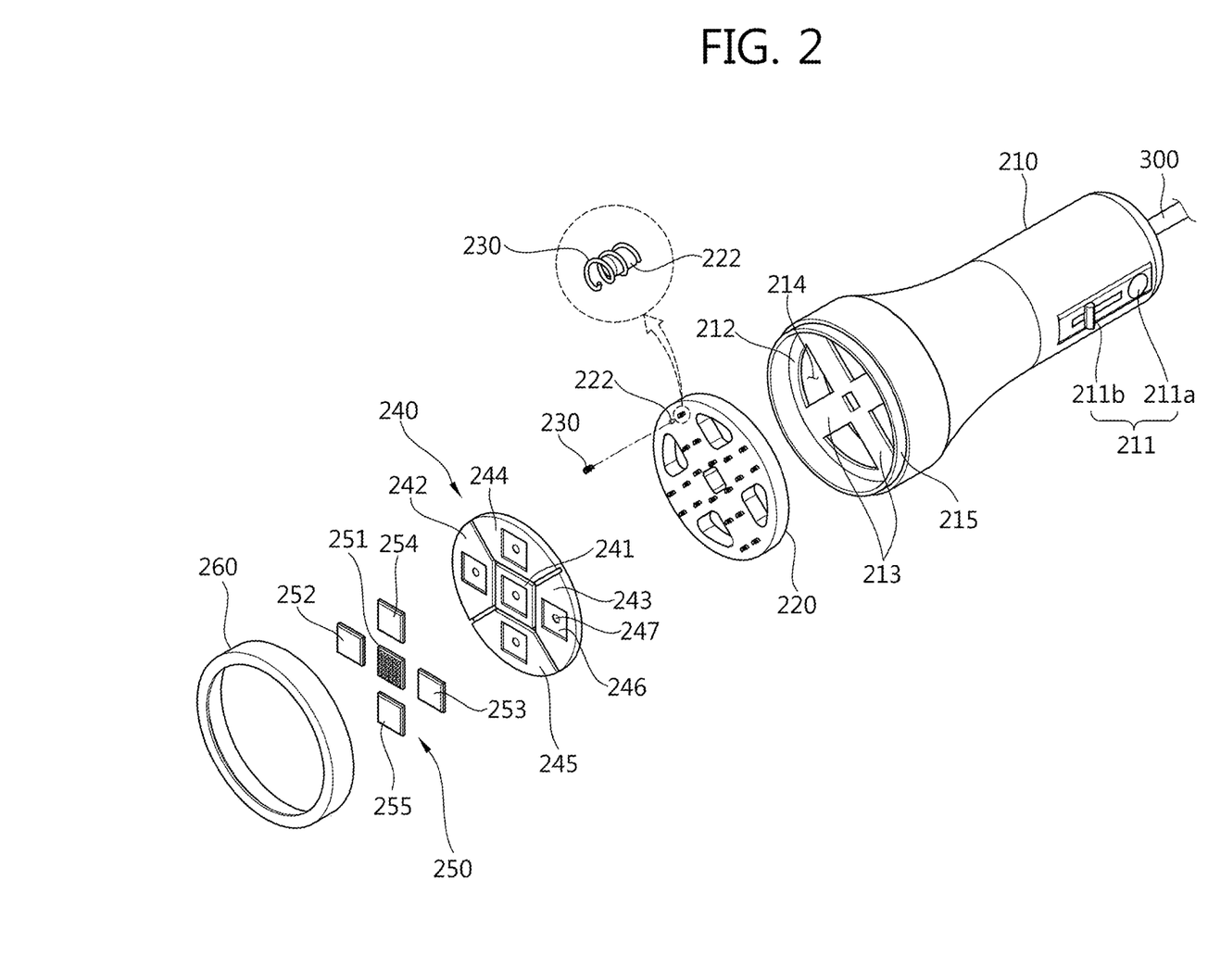
FIG. 2 is an exploded perspective view showing a handpiece of the treatment device using a radio frequency according to the first embodiment of the present invention.

FIG. 2 is an exploded perspective view showing the hand piece of the treatment device using a radio frequency according to the first embodiment of the present invention.

As shown in FIG. 2, the handpiece 200 of the treatment device 100 using a radio frequency according to the first embodiment of the present invention may have a body 210, an elastic member support 220, an electrode mount 240, an elastic member 230 between the elastic member support 220 and the electrode mount 240, an electrode unit 250, and a rim 260.

Figure 3:
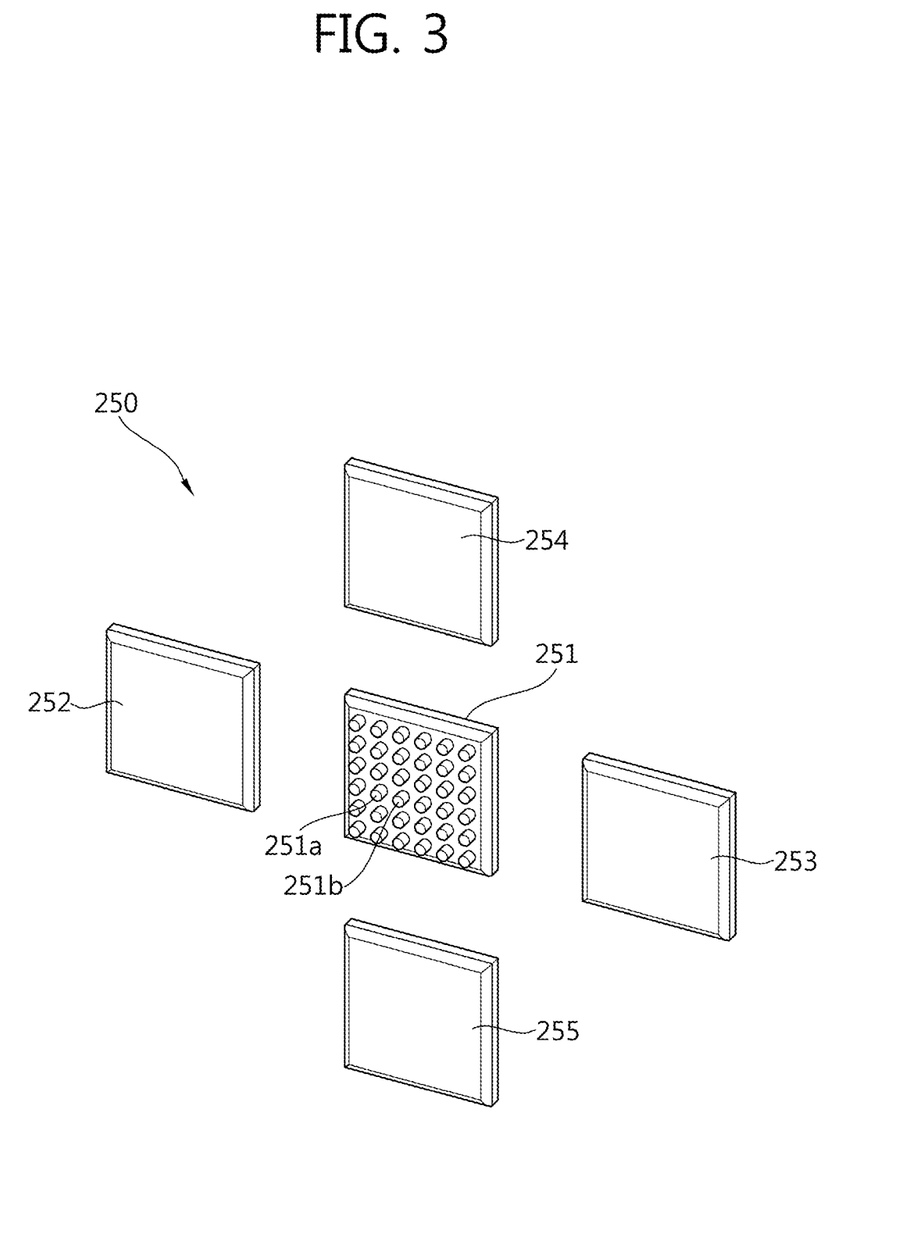
FIG. 3 is a perspective view showing an electrode unit of the treatment device using a radio frequency according to the first embodiment of the present invention.

FIG. 3 is a perspective view showing the electrode unit of the treatment device using a radio frequency according to the first embodiment of the present invention.

As shown in FIG. 3, the electrode unit 250 may include a first electrode module 251 at the center, second electrode modules 252 and 253 separated left and right from the first electrode module, and third electrode modules 254 and 255 separated over and under the first electrode module.

The first electrode module 251 may have a plurality of protruding electrodes 251a and 251b. The ends of the protruding electrodes 251a and 251 may be formed in a spherical shape or a flat shape, or in various shapes that can form a contact side with the surface of a skin.

Some of the protruding electrodes 251a and 251b may be anodes 251a and the others may be cathodes 251b. The numbers of the anodes 251a and 251b may be the same and the anodes 251a and the cathodes 251b may be alternately arranged.

The second electrode modules 252 and 253 may have an anode 252 and a cathode 253 at the left and right sides from the first electrode module 251. When the anode 252 is disposed at the left side, the cathode 253 may be disposed at the right side, or when the anode 252 is disposed at the right side, the cathode 253 may be disposed at the left side.

The third electrode modules 254 and 255 may have an anode 254 and a cathode 255 over and under the first electrode module 251. When the anode 254 is disposed at the upper side, the cathode 255 may be disposed at the lower side, or when the anode 254 is disposed at the lower side, the cathode 255 may be disposed at the upper side.

In this configuration, the radio frequency generator 140 of the body 100 includes a first radio frequency generation module 141 (see FIG. 8), a second radio frequency generation module 142 (see FIG. 8), and a third radio frequency generation module 143 (see FIG. 8), in which the first radio frequency generation module 141 is connected with the first electrode module 251, the second radio frequency generation module 142 is connected with the second electrode modules 252 and 253, and the third radio frequency generation module 143 is connected with the third electrode modules 254 and 255, such that they can transmit different RF energies to the electrode modules 251 to 255, respectively.

The electrode modules 251 to 255 can make independent circuits with a skin as a medium by making the radio frequencies transmitted to the electrode modules 251 to 255 different. That is, a RF current at a first frequency from the anode 251a of the first electrode module 251 flows to the cathode 251b of the first electrode module 251, a RF current at a second frequency from the anode 252 of the second electrode modules 252 and 253 flows to the cathode 253 of the second electrode modules 252 and 253, and a RF current at a third frequency from the anode 254 of the third electrode modules 254 and 255 flows to the cathode 255 of the third electrode modules 254 and 255.

Further, a plurality of anodes 251a and cathodes 251b of the first electrode module 251 are densely arranged, the anodes 252 and the cathode 253 of the second electrode modules 252 and 253 are disposed left and right from the first electrode module 251, and the anode 254 and the cathode 255 of the third electrode modules 254 and 255 are disposed over and under the first electrode module 251, such that the depth of the RF energy from the first electrode module 251 and the depth of the RF energy from the second electrode modules 252 and 253 and the third electrode modules 254 and 255 can be made different, the RF energy from the first electrode module 251 can be transmitted in various directions and the RF energies from the second electrode modules 252 and 253 and the third electrode modules 254 and 255 can be transmitted across each other with the first electrode module 251 therebetween.

Alternatively, the second electrode modules 252 and 253 and the third electrode modules 254 and 255 may receive RF energies at the same frequency. To this end, the second radio frequency generation module 142 and the third radio frequency generation module 143 may generate RF energies at the same frequency, or the second electrode modules 252 and 253 and the third electrode modules 254 and 255 may receive energy from one radio frequency generation module.

Figure 4:
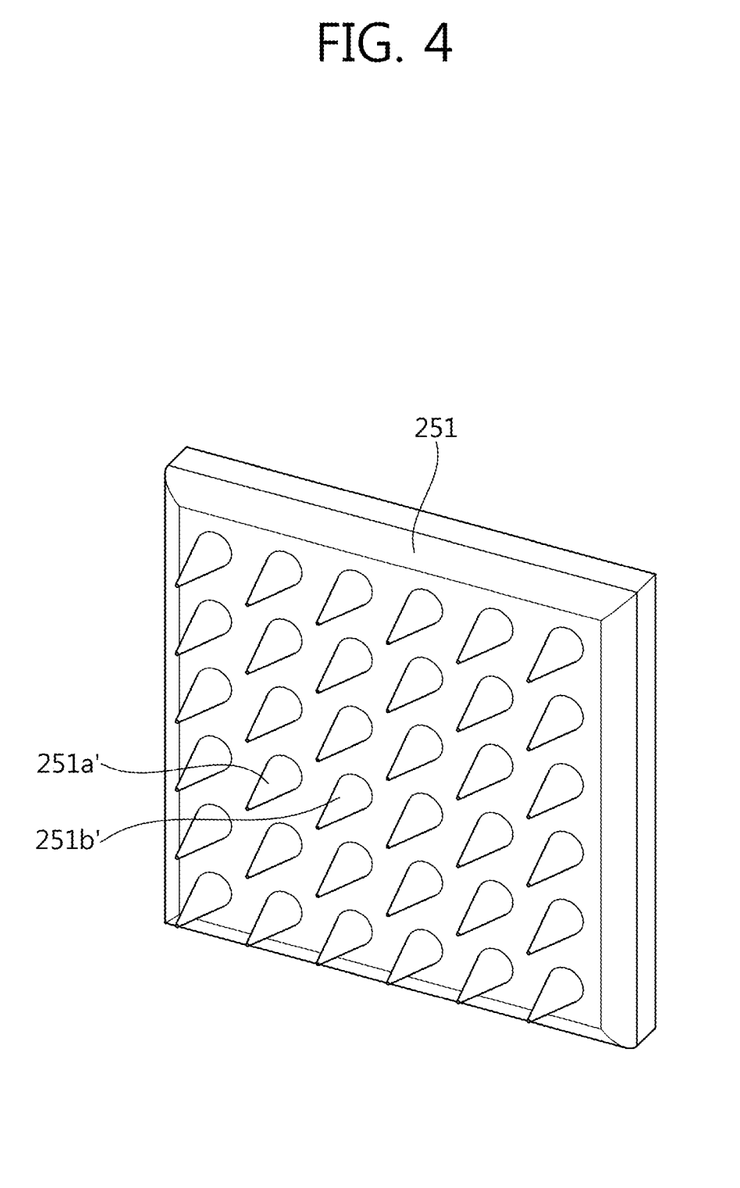
FIG. 4 is an exploded perspective view showing an invasive first electrode module of the treatment device using a radio frequency according to the first embodiment of the present invention.

FIG. 4 is an exploded perspective view showing an invasive first electrode module of the treatment device using a radio frequency according to the first embodiment of the present invention.

As shown in FIG. 4, a plurality of protruding electrodes 251a' and 252b' of the first electrode module 251 may be formed in the shape of a needle.

The example shown in FIG. 3 allows an operation with the protruding electrodes 251a and 251b of the first electrode module 251 in contact with the surface of a skin, but the example shown in FIG. 4 allows an operation with the ends of the protruding electrodes 251a' and 251b' of the first electrode module 251 inserted inside the skin surface. In this case, invasive treatment is performed on the skin surface, the effect of the skin treatment can be more improved.

Figure 5:
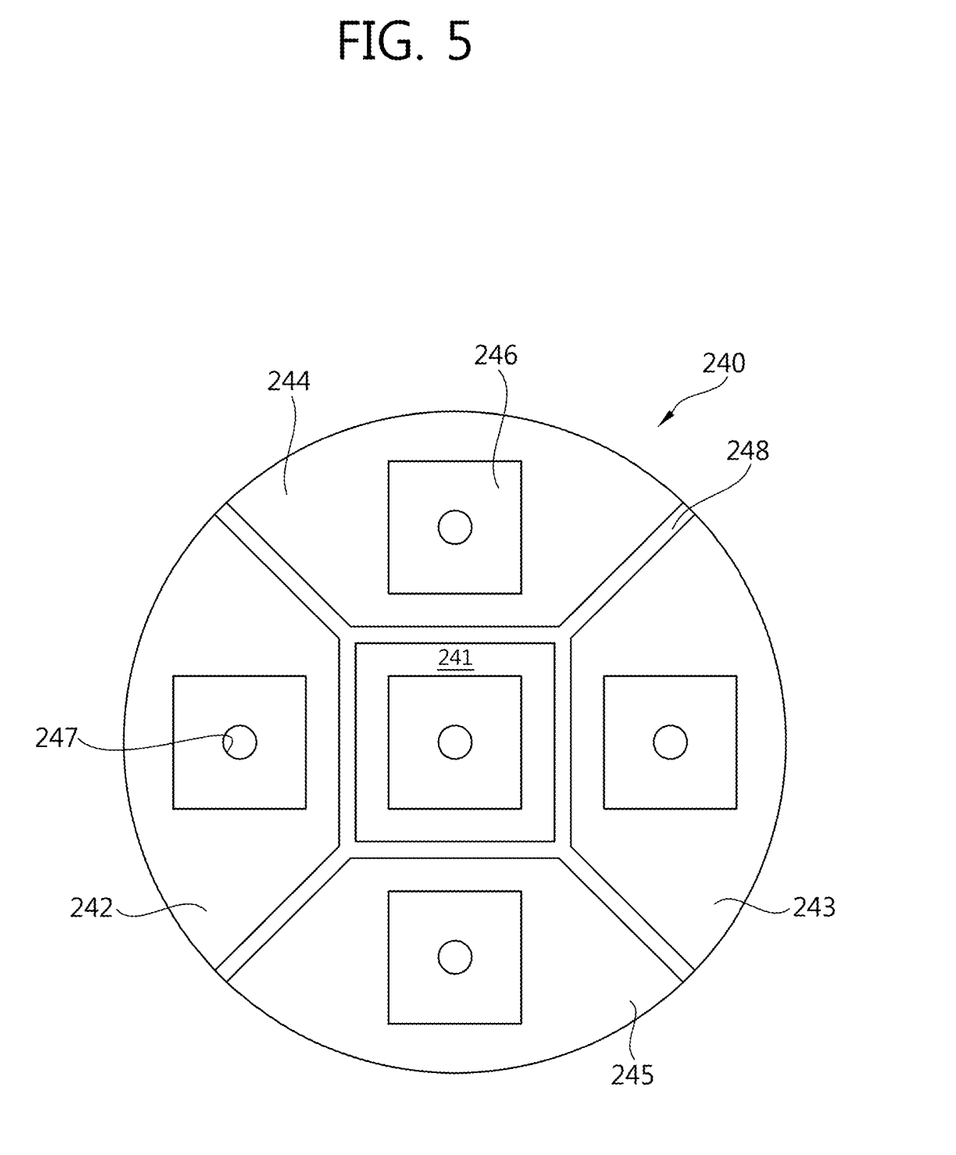
FIG. 5 is a plan view showing an electrode mount of the treatment device using a radio frequency according to the first embodiment of the present invention.

FIG. 5 is a plan view showing an electrode mount of the treatment device using a radio frequency according to the first embodiment of the present invention.

As shown in FIGS. 2 to 5, the electrode mount 240 of the treatment device 10 using a radio frequency according to the first embodiment of the present invention includes a plurality of pads 241 to 245 where the first electrode module 251, the second electrode modules 252 and 253, and the third electrode modules 254 and 255 are seated.

The pads 241 to 245 may be composed of a center pad 241 at the center where the first electrode module 251 is seated, a left pad 242 and a right pad 243 where the second electrode modules 252 and 253 are seated, and an upper pad 244 and a lower pad 245 where the third electrode modules 245 and 255 are seated.

The anode 252 and the cathode 253 of the second electrode modules 252 and 253 can be seated on the left pad 242 and the right pad 243, and the anode 254 and the cathode 255 of the third electrode modules 254 and 255 can be seated on the upper pad 244 and the lower pad 255.

Mounting grooves 246 may be formed at the pads 241 to 245 where the electrode modules 251 to 255 are inserted.

A through-hole 247 may be formed through the bottom of the mounting groove 246. The through-holes 247 may extend or diverge from the cable 300 to connect the transmitting lines 310 (see FIG. 8) for transmitting RF energy to the electrode modules 251 to 255 in the corresponding mounting grooves 246 and/or the signal line 320 (see FIG. 8) for transmitting various control signals to the electrode modules 251 to 255.

Alternatively, circuit boards (not shown) transmitting the RF energy transmitted through the cable 300 to the electrode modules 251 to 255 in the corresponding mounting grooves 246 may be further disposed on the bottoms of the mounting grooves 246.

In this configuration, the circuit board can be connected with the transmitting lines 310 and/or the signal line through the through-holes 247 and the electrode modules 251 to 255 can receive RF energy through the circuit boards.

On the other hand, the pads 241 to 245 may be connected with adjacent pads 241 to 245 by flexible elastic portions 248. The flexible elastic portions 248 may be made of a synthetic resin-based material having elasticity rapidly returning to the initial shape when an external force is removed, even if they are deformed such as bending by the external force.

When the electrode mount 240 with the electrode modules 251 to 255 is deformed and some of the pads 241 to 245 are pressed on a part with many convex curves of a human body, the pads around connected by the flexible elastic portions 248 surround the part of the human body, such that the electrode modules 251 to 255 can be efficiently brought in contact with the part of the human body.

An elastic member 230 is disposed on the other side of each of the pads 241 to 245 and the elastic members 230 can elastically support the pads 241 to 245 by being supported by the elastic member support 220 to be described below.

Figure 6:
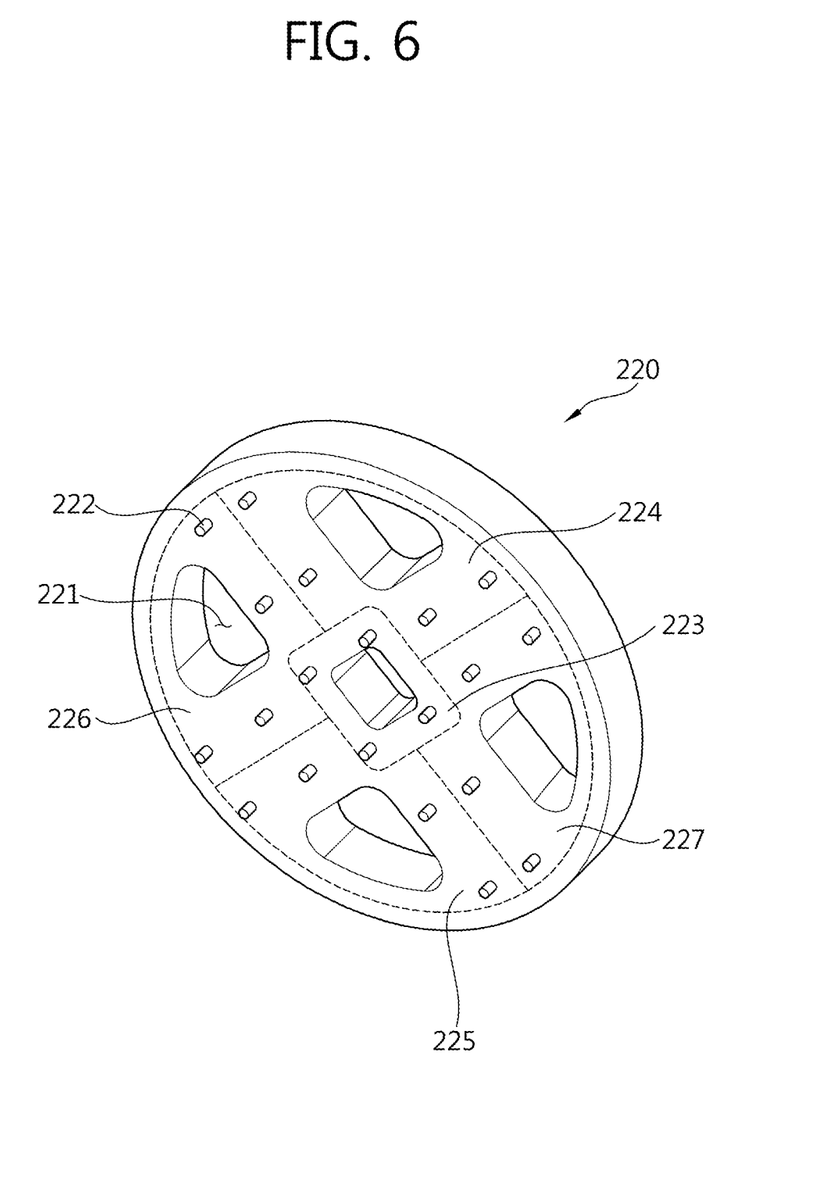
FIG. 6 is a plan view showing an elastic member support of the treatment device using a radio frequency according to the first embodiment of the present invention.

FIG. 6 is a plan view showing an elastic member support of the treatment device using a radio frequency according to the first embodiment of the present invention.

As shown in FIG. 6, the elastic member support 220 may have an outline similar to that of the electrode mount 240. For example, when the outline of the electrode mount 240 is a circle, the elastic member support 220 may have a circular outline with a diameter similar to that of the electrode mount 240, as shown in FIG. 6.

At least one or more connecting holes 221 corresponding to the through-holes 247 at the pads 241 to 245 of the electrode mount 240 may be formed through the elastic member support 220. The connecting holes 221 allow the cable 300 or the transmitting lines 310 (see FIG. 8) extending or diverging from the cable 300 and transmitting RF energy and/or the signal line 320 (see FIG. 8) transmitting various control signals to pass through them.

A plurality of elastic member support pins 222 correspond to the regions 223 to 227 of the pads may be formed on one side of the elastic member support 220. For example, as shown in FIG. 6, the elastic member support pins 222 may be arranged in a rectangular shape in the region 223 corresponding to the center pad 241 and may be arranged to correspond to the corners of the pads 242 and 243 in the regions 224, 225, 226, and 227 corresponding to the upper pad 244, the lower pad 245, the left pad 242, and the right pad 243, respectively.

Since the elastic member support pins 222 are arranged, as shown in FIG. 6, the elastic members 230 can firmly elastically support the pads 241 to 245, even if the pads 241 to 245 are moved in different directions by curves on a human body.

On the other hand, as shown in FIG. 2, the elastic member support 220 may be inserted and fixed inside the handpiece 200. In this configuration, a protruding support step 212 may be formed on the inner side of the handpiece 200 and at least one of support bars 213 radially extending from the support step 212 may be formed to more firmly support the elastic member support 220. Second connecting holes 214 corresponding to the connecting holes 221 may be formed at the support bars 212 and/or the support step 213.

Alternatively, the elastic member support 220 may be formed integrally with the handpiece 200.

The elastic member support 220 is formed in the handpiece 200 and the elastic members 230 are mounted on the elastic member support pins 222 of the elastic member support 220, respectively. The elastic members 230 may be coil springs having a restoring force against force that compresses the elastic members 230.

The electrode mount 240 is disposed such that one end of each of the elastic members 230 is in contact with the other side of each of the pads 241 to 245. Elastic member grooves where ends of the elastic members 230 are fitted or support pins similar to the elastic member support pins 222 of the elastic member support 220 may be formed on the other sides of the pads 241 to 245 in order to firmly and elastically support the pads 241 to 245 to the elastic members 230 even if they are moved by curves of a human body.

The electric modules 251 to 255 are disposed on the pads 241 to 245, respectively. When the mounting grooves 246 are formed on the pads 241 to 245, the electrode modules 251 to 255 are inserted in the mounting grooves 246. One side of each of the electrode modules 251 to 255 may protrude further than one end of the handpiece 200.

A rim 260 that supports the edge of the electrode mount 240 may be further provided to firmly fix the electrode mount 240 to the handpiece 200. The rim 260 may be fitted in a groove 215 formed around the outer side of one end of the handpiece 200.

Figure 7:
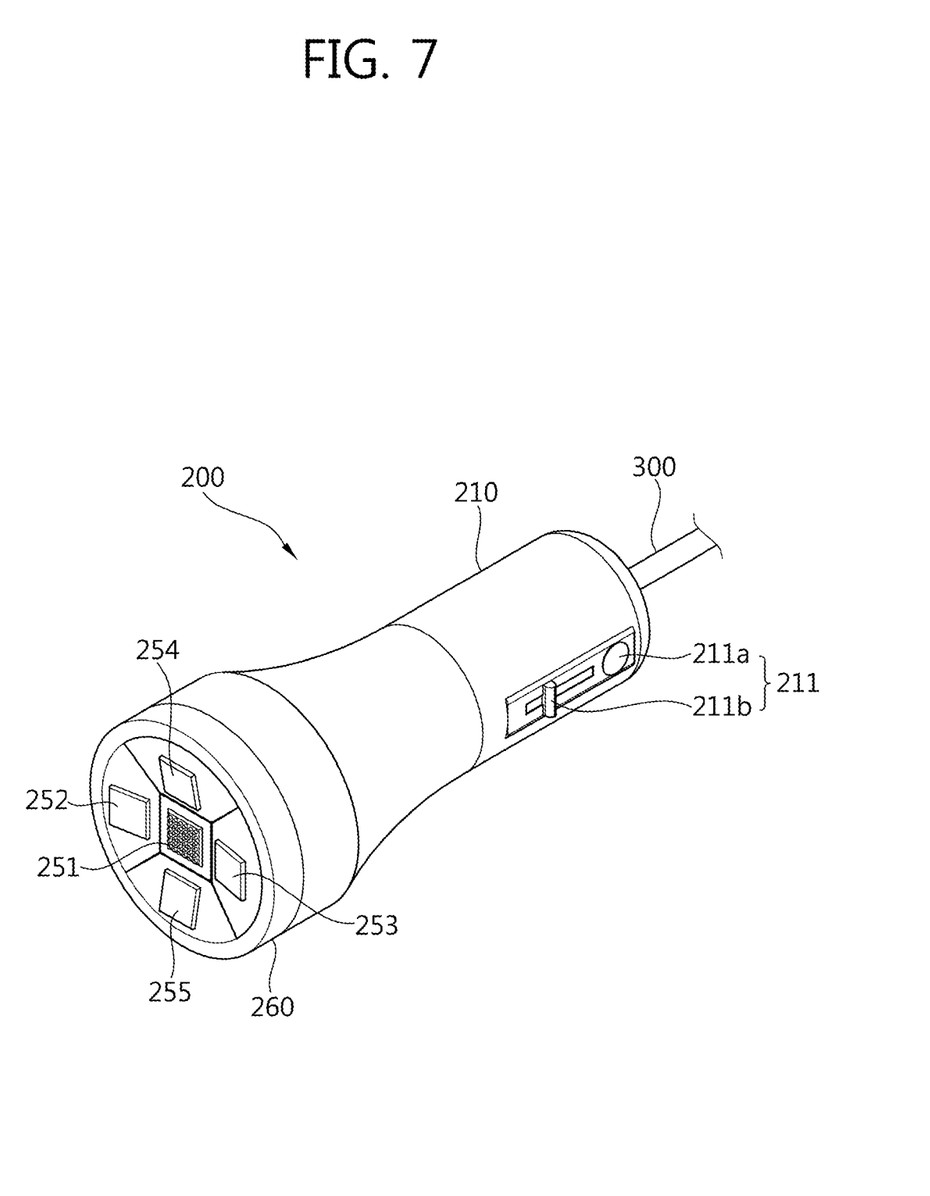
FIG. 7 is a view showing an example of use of the treatment device using a radio frequency according to the first embodiment of the present invention.

FIG. 7 is a view showing an example of use of the treatment device using a radio frequency according to the first embodiment of the present invention.

As shown in FIG. 7, when the handpiece 200 is used for a part with many curves due to the frame of a human body such as the face, the electrode mount 240 with the pads 241 to 245 deforms along the curves such that the electrode modules 251 to 255 are brought in close contact with the skin, such that treatment can be efficiently achieved.

Figure 8:
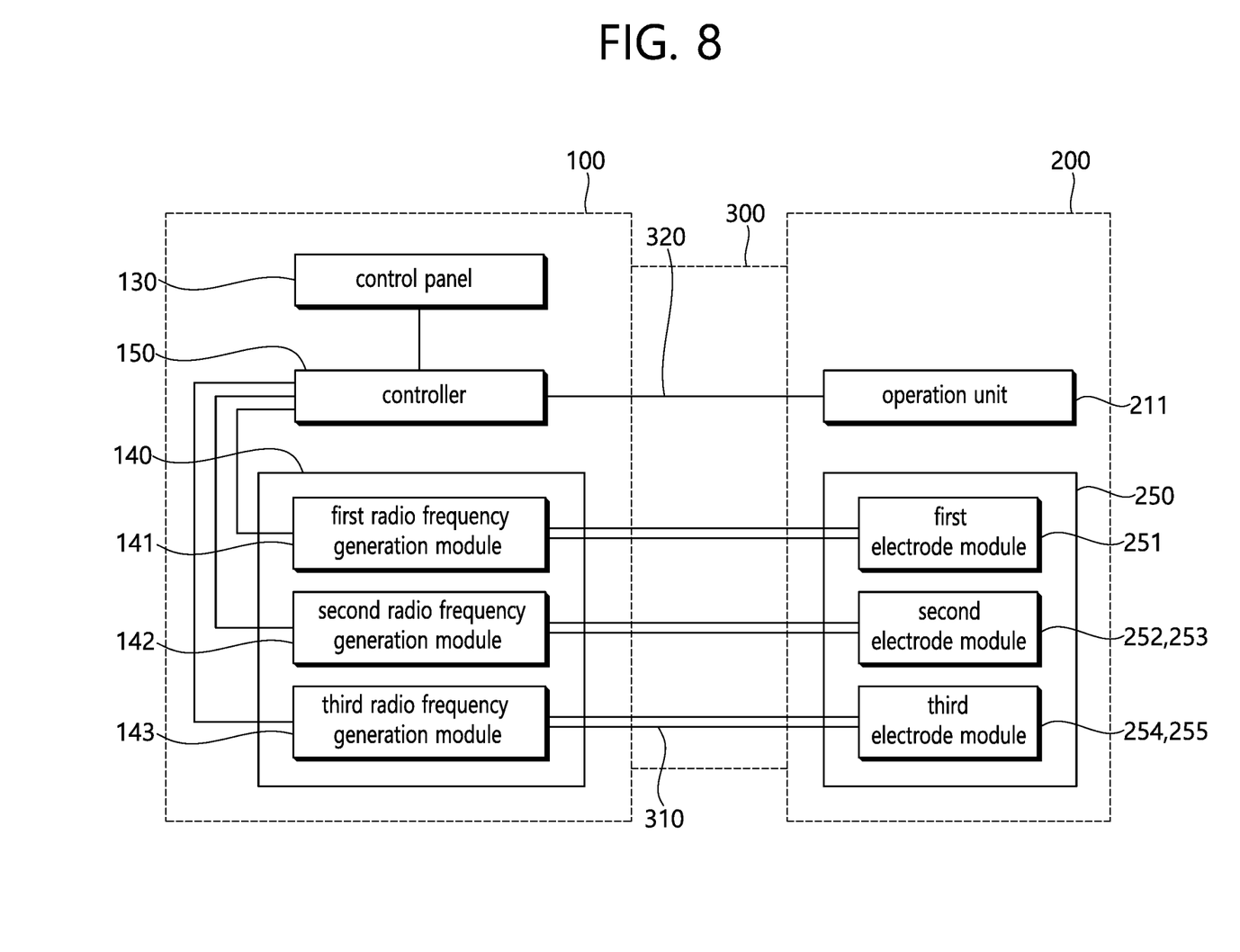
FIG. 8 is a block diagram showing the treatment device using a radio frequency according to the first embodiment of the present invention.

FIG. 8 is a block diagram showing the treatment device using a radio frequency according to the first embodiment of the present invention.

As shown in FIG. 8, the treatment device 10 using a radio frequency according to the first embodiment of the present invention includes a body 100 and a handpiece 200.

The body 100 includes a control panel 130, a radio frequency generator 140, and a controller 150 and the handpiece 200 may include an electrode unit 250 and an operation unit 211.

The radio frequency generator 140 may include a first radio frequency generation module 141, a second radio frequency generation module 142, and a third radio frequency generation module 143, which generate different radio frequencies.

The electrode unit 250 may include a first electrode module 251 connected to the first radio frequency generation module 141, second electrode modules 252 and 253 connected to the second radio frequency generation module 142, and third electrode modules 254 and 255 connected to the third radio frequency generation module 143.

Accordingly, the radio frequency generator 140 can transmit RF energy at different frequencies from the radio frequency generation modules 141 to 143 to the electrode modules 251 to 255 through transmitting lines 310, respectively, and the RF energies at the frequencies can be provided to a skin tissue through the corresponding modules 251 to 255, respectively.

The controller 150 can control the frequency and/or output of RF energy by controlling the radio frequency generation modules 140 in accordance with the details that the user inputs through the control panel 130 or through the operation unit 211 or modes stored in advance. The details inputted through the operation unit 211 can be transmitted to a signal line 320 connecting the controller 150 with the operation unit 211.

A treatment device using a radio frequency according to the second embodiment of the present invention is described in detail hereafter. For the convenience of description, the parts similar to those of the first embodiment are indicated by the same reference numerals and the same configuration as that of the first embodiment is not described.

Figure 9:
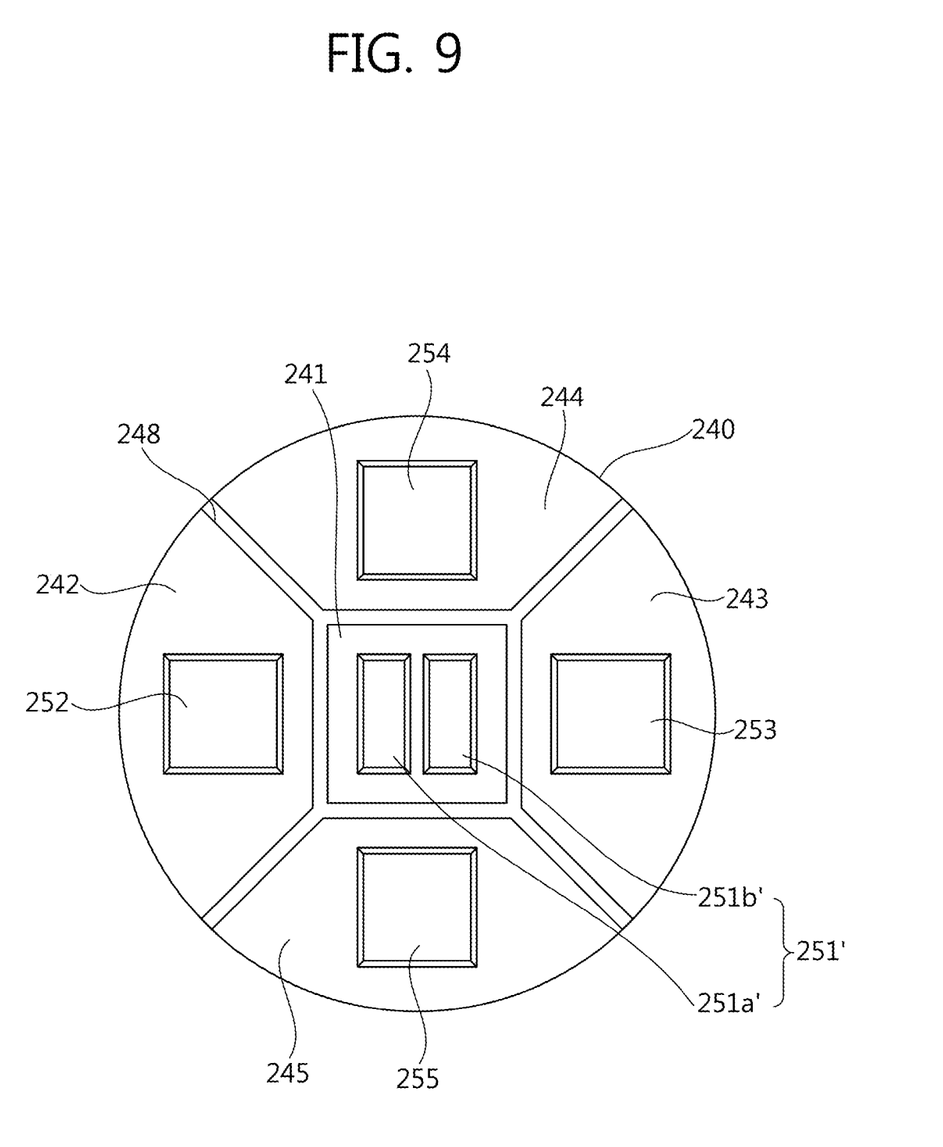
FIG. 9 is a plan view showing an electrode mount and an electrode unit of a treatment device using a radio frequency according to the second embodiment of the present invention.

FIG. 9 is a plan view showing an electrode mount and an electrode unit of a treatment device using a radio frequency according to the second embodiment of the present invention.

Although the first electrode module 251 is composed of a plurality of protruding electrodes in the electrode unit 250 of the treatment device 10 using a radio frequency according to the first embodiment of the present invention, a first electrode module 251' of the treatment device using a radio frequency according to the second embodiment of the present invention is composed of an anode 251a' and a cathode 251b' that are adjacent to each other.

In the electrode unit 250 according to the second embodiment of the present invention, similar to the electrode unit 250 according to the first embodiment of the present invention, the gap between the anode 251a' and the cathode 251b' of the first electrode module 251' is different from the gap between the anodes 252 and 254 and the cathodes 253 and 255 of the second electrode modules 252 and 253 and the third electrode modules 254 and 255, such that the depths of a skin to which RF energies are transmitted can be made different, but unlike the electrode unit 250 according to the first embodiment of the present invention, the RF energy by the first electrode module 251' can be transmitted to the anode 251a' and the cathode 251b', not in various directions.

Though not shown, it is possible to make the traveling directions of the RF energies by the electrode modules 251' to 255 different by arranging the anode 251a' and the cathode 251b' of the first electrode module 251' orthogonally to the anodes 252 and 254 and the cathodes 253 an 255 of the second electrode modules 252 and 253 and the third electrode modules 254 and 255.

A treatment device using a radio frequency according to the third embodiment of the present invention is described in detail hereafter. For the convenience of description, the parts similar to those of the first embodiment are indicated by the same reference numerals and the same configuration as that of the first embodiment is not described.

Figure 10:
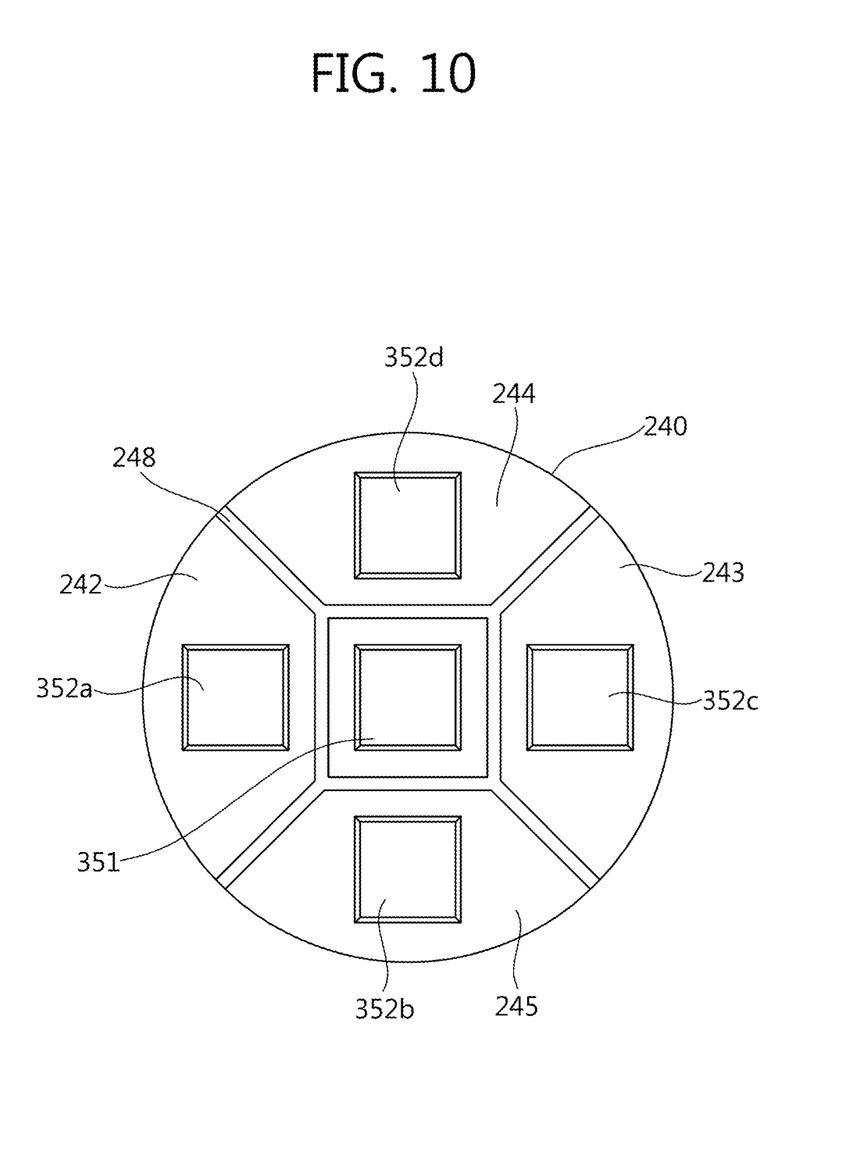
FIG. 10 is a plan view showing an electrode mount and an electrode unit of a treatment device using a radio frequency according to the third embodiment of the present invention.

FIG. 10 is a plan view showing an electrode mount and an electrode unit of a treatment device using a radio frequency according to the third embodiment of the present invention.

Although the electrode module 250 of the treatment device 100 using a radio frequency according to the first embodiment of the present invention includes a plurality of electrode modules 251 to 255 transmitting RF energies at different frequencies, electrode units 351 and 352a to 352d of the treatment device using a radio frequency according to the third embodiment transmit RF energies at a single frequency.

An anode 351 may be disposed at a center pad 241 and cathodes 352a to 352d may be disposed at an upper pad 244, a lower pad 245, a left pad 242, and a right pad 243. In contrast, a cathode may be disposed at the center pad 241 and anodes may be disposed at the upper pad 244, the lower pad 245, the left pad 242, and the right pad 243.

A radio frequency generator 140 in the body 100 may also have a single radio frequency generation module.

A treatment device using a radio frequency according to the fourth embodiment of the present invention is described in detail hereafter. For the convenience of description, the parts similar to those of the first embodiment are indicated by the same reference numerals and the same configuration as that of the first embodiment is not described.

Figure 11:
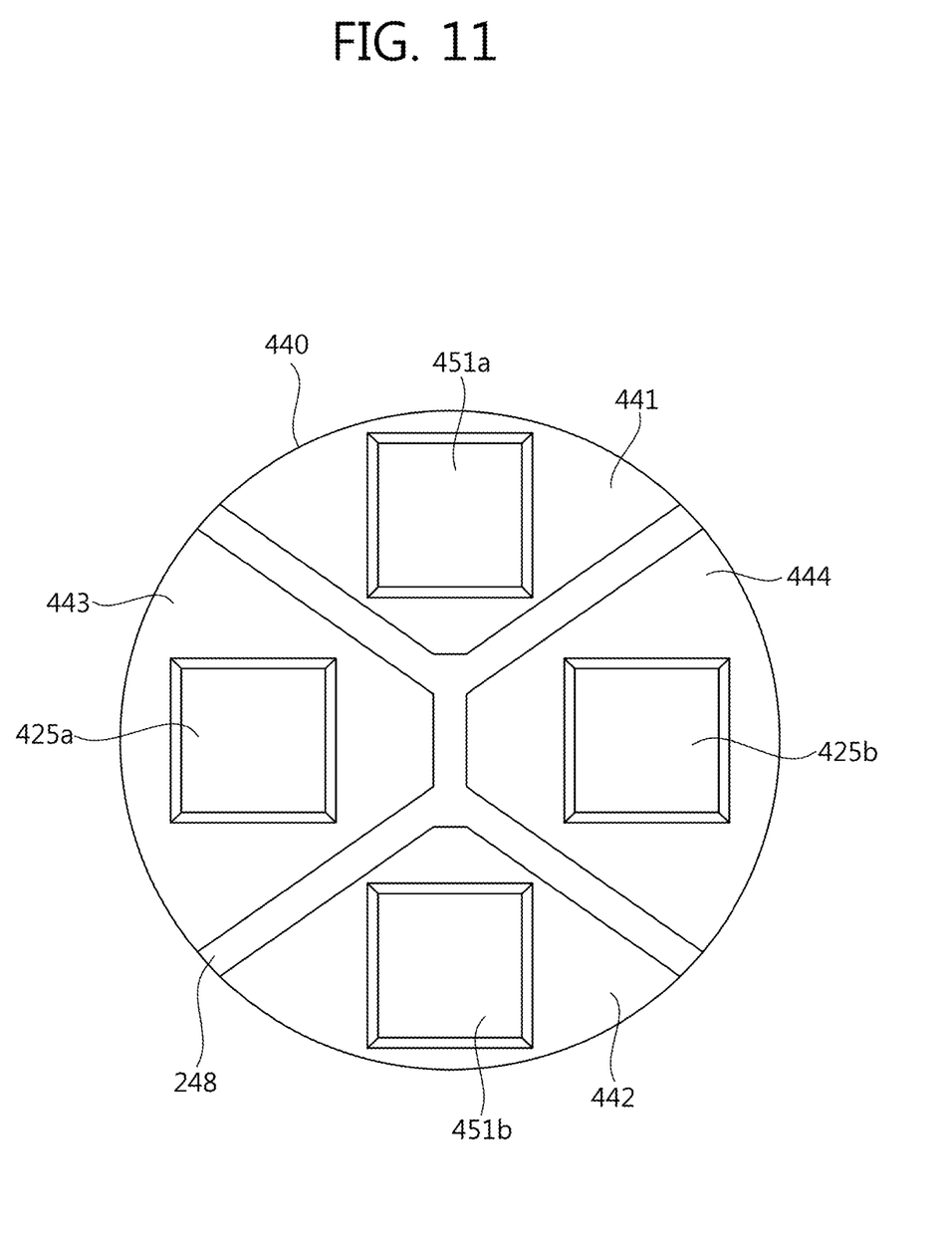
FIG. 11 is a plan view showing an electrode mount and an electrode unit of a treatment device using a radio frequency according to the fourth embodiment of the present invention.

FIG. 11 is a plan view showing an electrode mount and an electrode unit of a treatment device using a radio frequency according to the fourth embodiment of the present invention.

Although the electrode unit 250 of the treatment device 10 using a radio frequency according to the first embodiment of the present invention includes the first electrode module 251 at the center and the electrode mount 240 includes the center pad 241 where the first electrode module 251 is disposed, the treatment device using a radio frequency according to the fourth embodiment of the present invention has no electrode or pad at the center.

An electrode mount 440 of the treatment device using a radio frequency according to the fourth embodiment of the present invention includes an upper pad 441, a lower pad 442, a left pad 443, and a right pad 444. Further, the electrode mount 440 according to this embodiment also has flexible elastic portions 248 such that adjacent pads 441 and 444 can be connected with each other by the elastic portions 248.

The electrode unit 250 of the treatment device using a radio frequency according to the fourth embodiment of the present invention may include first electrode modules 451a and 451b separately disposed at thee upper pad 441 and the lower pad 442 and second electrode modules 452a and 452b separately disposed at the left pad 443 and the right pad 444.

The first electrode modules 451a and 451b may include an anode 451a and a cathode 451b disposed at the upper pad 441 and the lower pad 442. When the anode 451a is disposed at the upper side, the cathode 451b may be disposed at the lower side, or when the anode 451a is disposed at the lower side, the cathode 451b may be disposed at the upper side.

The second electrode modules 452a and 452b may include an anode 452a and a cathode 452b disposed at the left pad 443 and the right pad 444. When the anode 452a is disposed at the left side, the cathode 452b may be disposed at the right side, or when the anode 452a is disposed at the right side, the cathode 452b may be disposed at the left side.

In this configuration, the radio frequency generator 140 includes a first radio frequency generation module 141 and a second radio frequency generation module 142, the first radio frequency generation module 141 is connected with the first electrode modules 451a and 451b, and the second radio frequency generation module 142 is connected with the second electrode modules 452a and 452b, such that different RF energies can be transmitted to the electrode modules 451a, 451b, 452a, and 452b.

Other than the embodiments described above, the present invention may be implemented in various embodiments, for example, in which the electrode unit is composed of a pair of anode and cathode or composed of three electrodes arranged in a triangle.

Since the pads where the electrodes are disposed can be inclined in different directions, contact of the electrodes can be efficiently maintained even in treatment for parts with many curves of a human body such as the face. Further, even if the handpiece is moved in contact with a skin, it can actively cope with curves and the pad can keep in contact with the skin.

An embodiment of the present invention described above with reference to the figures should not be construed as limiting the spirit of the present invention. The protective range of the present invention is limited only by the claims and the spirit of the present invention may be changed and modified in various ways by those skilled in the art. Accordingly, the changes and modifications would be included in the protective range of the present invention, as long as they are apparent to those skilled in the art.

The invention claimed is:

1. A treatment device using a radio frequency, comprising:
a plurality of electrodes that transmit RF energy to a skin;
a plurality of pads where at least one or more of the electrodes are disposed on one side of the plurality of pads
a plurality of connecting portions disposed between the pads and connecting the pads bendably;
a plurality of elastic members that independently and elastically support a second side of the pads,
wherein the electrodes can be three-dimensionally brought in close contact with a curved skin by combined movement of the pad by the connecting portion and the plurality of elastic members.

2. The treatment device of claim 1, wherein the pad has a mounting groove on one side where the electrode is disposed.

3. The treatment device of claim 1, wherein the pads include a center pad at the center and peripheral pads around the center pad.

4. The treatment device of claim 3, wherein the electrodes include a first electrode and second electrodes which have different polarities, the first electrode is disposed on the center pad, and the second electrodes are disposed on the peripheral pads.

5. The treatment device of claim 4, wherein the electrodes include a first electrode module, a second electrode module, and a third electrode module which provide RF energies at different frequencies,
an anode and a cathode of the first electrode module are disposed on the center pad,
an anode and a cathode of the second electrode module are disposed on the pads, which are positioned left and right from the center pad, respectively, in the peripheral pads, and
an anode and a cathode of the third electrode module are disposed on the pads, which are positioned over and under the center pad, respectively, in the peripheral pads.

6. The treatment device of claim 4, wherein the electrodes include a first electrode module and a second electrode module which provide RF energies at different frequencies, wherein an anode and a cathode of the first electrode module are disposed on the center pad, and an anode and a cathode of the second electrode module are disposed on the peripheral pads.

7. The treatment device of claim 1, wherein the pads include an upper pad, a lower pad, a left pad, and a right pad.

8. The treatment device of claim 7, wherein the electrodes include a first electrode module and a second electrode module which provide RF energies at different frequencies, wherein an anode and a cathode of the first electrode module are disposed on the upper pad and the lower pad, and an anode and a cathode of the second electrode module are disposed on the left pad and the right pad.

9. The treatment device of claim 1, wherein the pads include a first pad and a second pad, the electrodes include a first electrode unit and a second electrode unit that have different polarities, the first electrode unit is disposed on the first pad, and the second electrode unit is disposed on the second pad.

10. The treatment device of claim 1, wherein the electrodes include a plurality of protruding electrodes of which the ends come in contact with a skin are formed in a spherical shape or a flat shape.

11. The treatment device of claim 1, wherein the electrodes include a plurality of protruding electrodes that have needle-shaped ends and is partially inserted into a skin.

12. The treatment device of claim 1, wherein the elastic members are coil springs having restoring force against compression force.

13. The treatment device of claim 1, further comprising an elastic member support that is spaced from the pads and elastically supports the elastic members.

14. The treatment device of claim 13, wherein a plurality of elastic member support pins where the elastic members are mounted is formed on one side of the elastic member support.

15. The treatment device of claim 1, wherein at least two elastic members of the plurality of elastic members independently and elastically support each of the pads.

16. The treatment device of claim 1, wherein each of the plurality of electrodes is seated in a respective one of the plurality of pads.

17. The treatment device of claim 1, wherein the plurality of connecting portion is made by flexible material.

18. A treatment device using a radio frequency, comprising:
a plurality of electrodes that transmit RF energy to a skin;
an electrode mount comprising,
a plurality of pads where at least one or more of the electrodes are disposed on one side of the plurality of pads, and
a plurality of connecting portions disposed between the pads and connecting the pads bendably;
a plurality of elastic members that independently and elastically support a second side of the pads,
wherein the electrode mount can deform to comply with a shape of a skin in close contact with the skin by combined movement of the pad by the plurality of connecting portions and the plurality of elastic members.

19. A treatment device using a radio frequency, comprising:
a body that comprises a radio frequency generator generating RF energy; and
a handpiece that comprises a plurality of electrodes electrically connected with the radio frequency generator and transmitting the RF energy to a skin, on one end,
wherein the handpiece comprises
an electrode mount comprising
a plurality of pads where the electrodes are disposed, and
a plurality of connecting portions disposed between the pads and connecting the pads bendably, and
a plurality of elastic members that independently and elastically supports the pads,
wherein the electrode mount can deform to comply with a shape of a skin in close contact with the skin by combined movement of the pad by the plurality of connecting portions and the plurality of elastic members.

* * * * *